United States Patent
Schafer et al.

(10) Patent No.: US 8,858,518 B2
(45) Date of Patent: Oct. 14, 2014

(54) CANISTER FOR AUTOLOGOUS FAT TRANSFER

(76) Inventors: Mark E. Schafer, Lower Gwynedd, PA (US); Wayne A. Siebrecht, Golden, CO (US); Constantino G. Mendieta, Miami, FL (US); Kevin J. Hight, Louisville, CO (US); Adnan I. Merchant, Fremont, CA (US)

( * ) Notice: Subject to any disclaimer, the term of this patent is extended or adjusted under 35 U.S.C. 154(b) by 0 days.

(21) Appl. No.: 13/402,778

(22) Filed: Feb. 22, 2012

(65) Prior Publication Data

US 2012/0271254 A1 Oct. 25, 2012

Related U.S. Application Data

(60) Provisional application No. 61/445,526, filed on Feb. 22, 2011.

(51) Int. Cl.
*A61M 1/00* (2006.01)
*A61B 10/00* (2006.01)

(52) U.S. Cl.
CPC ......... *A61M 1/0005* (2013.01); *A61M 2202/08* (2013.01); *A61M 1/0007* (2014.02); *A61M 1/0023* (2013.01); *A61M 2205/7527* (2013.01); *A61B 10/0045* (2013.01)
USPC ............ 604/319; 604/317; 604/540; 604/542

(58) Field of Classification Search
None
See application file for complete search history.

(56) References Cited

U.S. PATENT DOCUMENTS

| | | | | |
|---|---|---|---|---|
| 3,719,197 A | * | 3/1973 | Pannier et al. | 137/205 |
| 3,768,478 A | * | 10/1973 | Fertik et al. | 604/320 |
| 4,321,139 A | * | 3/1982 | Auclair | 210/232 |
| 4,439,319 A | * | 3/1984 | Rock | 210/238 |
| 4,460,361 A | * | 7/1984 | Nichols | 604/319 |
| 4,809,860 A | * | 3/1989 | Allen | 220/502 |
| 4,870,975 A | | 10/1989 | Cronk et al. | |
| 5,055,198 A | * | 10/1991 | Shettigar | 210/650 |
| 5,108,381 A | | 4/1992 | Kolozsi | |
| 5,624,418 A | * | 4/1997 | Shepard | 604/319 |
| 5,807,358 A | * | 9/1998 | Herweck et al. | 604/320 |
| 8,100,874 B1 | * | 1/2012 | Jordan et al. | 604/319 |
| 8,172,832 B1 | * | 5/2012 | Gonzalez | 604/542 |
| 2002/0026212 A1 | * | 2/2002 | Wholey et al. | 606/200 |
| 2008/0209709 A1 | | 9/2008 | Mayer | |

(Continued)

OTHER PUBLICATIONS

PCT International Search Report and Written Opinion in International Application PCT/US2012/026171, mailed Jun. 5, 2012, 8 pgs.

(Continued)

*Primary Examiner* — Tan-Uyen T Ho
*Assistant Examiner* — Eric Bryant
(74) *Attorney, Agent, or Firm* — BENNETT Intellectual Property; Allen F. Bennett

(57) ABSTRACT

Described are embodiments of a canister, system, and method of filtering fat. Embodiments include a sidewall that defines a volume, a filter with a screen, a first port, a second port, and at least one vane which allows for manual agitation of lipoaspirate within the volume. The first port is used to draw fluid from below the filter, forcing excess fluid in the lipoaspirate to be quickly extracted. The vane allows the lipoaspirate to be repeatedly drawn over the filter to aide in removing of liquids from fat in the lipoaspirate. The treated fat may then be removed from the volume through an outlet port and reinjected into a patient.

17 Claims, 13 Drawing Sheets

(56) References Cited

U.S. PATENT DOCUMENTS

| | | | |
|---|---|---|---|
| 2009/0112157 A1* | 4/2009 | Jessop | 604/91 |
| 2009/0287190 A1 | 11/2009 | Shippert | |
| 2010/0106108 A1* | 4/2010 | Hirsch | 604/290 |
| 2010/0152648 A1* | 6/2010 | Andersohn | 604/35 |

OTHER PUBLICATIONS

Adnan I. Merchant, U.S. Appl. No. 29/407,729 entitled "CANISTER", filed Dec. 1, 2011.

* cited by examiner

CANISTER FOR AUTOLOGOUS FAT TRANSFER

CROSS-REFERENCE TO RELATED PATENT APPLICATIONS

This application claims priority to U.S. Provisional Patent Application No. 61/445,526, filed Feb. 22, 2011, entitled CANISTER FOR AUTOLOGOUS FAT TRANSFER, which is hereby incorporated by reference in its entirety as if set forth herein in full.

FIELD OF THE INVENTION

The technical field is surgical equipment; specifically a canister used for the harvesting and transfer of fat tissue such as Autologous Fat Transfer.

BACKGROUND OF THE INVENTION

In aesthetic body contouring, it is sometimes desirable to transfer fat tissue from one portion of the body where it is excessive, unwanted, or unsightly, to another portion of the body where that same fat may be considered more appropriate or appealing. For instance, fat may be removed from a patient's abdominal, hip, or thigh region; it may be desirable to transfer this fat to the buttocks, breast, or bicep region, depending upon the patient. The transfer of fat from one region of a patient's body to another is commonly termed Autologous Fat Transfer or AFT.

The most common approach to fat removal is liposuction, which first involves the infiltration of fluid into a selected region of the body. The infiltrated fluid, comprising primarily a saline solution with an anesthetic (typically lidocaine) and a vasoconstrictor (typically epinephrine), serves several purposes. The bulk saline solution serves to expand the fat tissue away from the connective matrix and provide a more conducive fluid condition for fat removal; the lidocaine reduces pain and patient discomfort (even when the patient is fully sedated and unconscious for the procedure); the epinephrine constricts the blood vessels, thereby reducing bleeding and lidocaine removal, and reduces swelling. Once the infiltration fluid has been introduced, the fat/fluid mixture is removed using a vacuum cannula. The cannula may also be mechanically actuated to assist in the removal; there may also be an intermediate step of applying ultrasound energy to the fat tissue (Ultrasound Assisted Lipoplasty or UAL) in order to fragment or emulsify the tissue to separate it from the connective tissue matrix.

The amount of fluid infiltrated into the patient is typically equal to, or more than, the expected amount of fat to be withdrawn. When the fat is removed by liposuction, it is in a lipoaspirate that includes remnant infiltration fluid, blood and other unwanted connective tissues. In this form, it is unsuitable for reinjection into the patient. A separation means must be provided to separate the wanted fat component from the overall lipoaspirate fluid before the fat component is reinjected into a patient.

To the extent possible, it is desirable that the process of harvesting, separating, and reinjecting take place under conditions approaching "aseptic," in order to prevent introduction of unwanted infectious or otherwise harmful material into the patient. The harvesting procedures have been well established, and the reinjection approaches have also been demonstrated, however the separation techniques have received less focus and provide an area to improve the overall AFT process.

A number of approaches have been attempted to solve the separation process issues. In the simplest approach, the lipoaspirate is allowed to sit in a harvest container for a period of time. The fat component, being less dense than either blood, freed oils, or saline, eventually floats to the top region of the container where it can be "decanted." This process however takes a relatively long amount of time, and the separation is rarely complete in that much of the fat remains in intimate mixture with the other components of the lipoaspirate for a period of time that is longer than the patient can safely remain under anesthesia.

Another method involves pouring the lipoaspirate into smaller centrifuge tubes, and centrifuging for a period of time (typically 3 minutes). This process more completely separates the fat cells from the other fluids. The centrifuge tubes can either be decanted into syringes, or, in some systems, capped syringe tubes are used within the centrifuge, eliminating one step in the process.

Another method involves pouring the lipoaspirate through a metal filter, capturing the fat in the filter. The fat is then manually scooped into syringe tubes.

Yet another method involves pouring the lipoaspirate onto a sterile absorbent pad (a "Telfa" pad), and manipulating the fat on the pad until the desired amount of fluid has been absorbed and the remaining fat is sufficiently "dry." This technique has been referred to as "Telfa rolling."

The above techniques involve exposing the lipoaspirate to the open environment, with manual handling and manipulation. Thus, they all suffer from an increased possibility of biological contamination. Furthermore, they generally are suited to batch operation, not continuous operation, and typically involve only small quantities of fat.

An alternative approach uses a container with a removal port at the bottom of the container, which eliminates the need to decant the fat. Instead, after the necessary settling time, the bottom valve is opened and the (heavier) blood/fluid is drawn off until only the fat remains. The port is then connected to an injection syringe and the fat is transferred for reinjection. A container for use in this technique is available commercially from Sound Surgical Technologies, Louisville, Colo. as the "Origins Lipo Harvesting System" canister.

Another approach involves placing a filter within a lipoaspirate container, such that the fat is captured and the unwanted liquids are conveyed to another (disposal) container. A system that uses this approach is sold by Shippert Medical, Colorado, under the Tissue-Trans and Filtron product names.

Another approach, called the PureGraft (sold by Cytori Therapeutics, Inc., San Diego, Calif.), involves pumping the lipoaspirate into a flexible plastic container with an internal filter. The fat is further processed by the introduction of additional saline solution, with manual agitation of the container. The result of this process is a relatively pure fat cell solution. However, the amount of fat processed is limited to the size of the flexible container, which is less than 500 cc. The PureGraft, as introduced to the market, is a flexible plastic pouch with an internal filter. The agitation is performed by manually squeezing the pouch. The product is therefore a disposable product because it cannot be effectively cleaned, although it may be used twice for the same patient. The design also limits the process to a small batch at a time. The technique does not handle fat removed using procedures such as power assisted lipoplasty (PAL) very well because of the large strands of fat removed in these types of procedures.

The last techniques mentioned above are "closed", i.e. not exposing the fat to the environment during processing. Nevertheless, these techniques involve "batch" processing. That is, the fat harvesting process must be complete before filling the syringe tubes for reinjection. The batch processing results in a prolonged AFT procedure.

The prior techniques and devices have various shortcomings, including long processing times; limited total fat processing capability; open system exposing the fat to the air; "batch" processing, i.e. a requirement to complete the fat harvesting process before filling the syringe tubes for reinjection.

It is with respect to these and other considerations that embodiments of the present invention have been made. Also, although relatively specific problems have been discussed, it should be understood that embodiments of the present invention should not be limited to solving the specific problems identified in the background.

SUMMARY

This summary is provided to introduce a selection of concepts in a simplified form that are further described below in the Detail Description section. This summary is not intended to identify key features or essential features of the claimed subject matter, nor is it intended to be used as an aid in determining the scope of the claimed subject matter.

Described are embodiments of the present invention. Features of some embodiments include a canister with a removable filter that includes a screen. The screen has, in embodiments, openings of between about 200 microns to about 1000 microns, such as about 432 microns, about 500 microns, or about 533 microns). The canister also includes, in embodiments, an aspiration port that directs lipoaspirate entering the canister to the side of the canister, a vacuum port, and at least one vane which allows for manual agitation of the fat within the canister while under aspiration vacuum. The vacuum port allows fluid to be drawn from below the filter, forcing excess fluid in the lipoaspirate to be quickly separated from the fat. The vane allows the lipoaspirate to be repeatedly drawn over the filter and deposited in a channel connected to an outlet port. In embodiments, the filtered fat can be extracted from the canister through the outlet port without breaking any seals and while the canister is under vacuum.

BRIEF DESCRIPTION OF THE DRAWINGS

Non-limiting and non-exhaustive embodiments are described with reference to the following figures.

DETAILED DESCRIPTION

Various embodiments are described more fully below with reference to the accompanying drawings, which form a part hereof, and which show specific exemplary embodiments for practicing the invention. However, embodiments may be implemented in many different forms and should not be construed as limited to the embodiments set forth herein; rather, these embodiments are provided so that this disclosure will be thorough and complete, and will fully convey the scope of the invention to those skilled in the art. Embodiments may be practiced as methods, systems or devices. The following detailed description is, therefore, not to be taken in a limiting sense.

Figure 1:
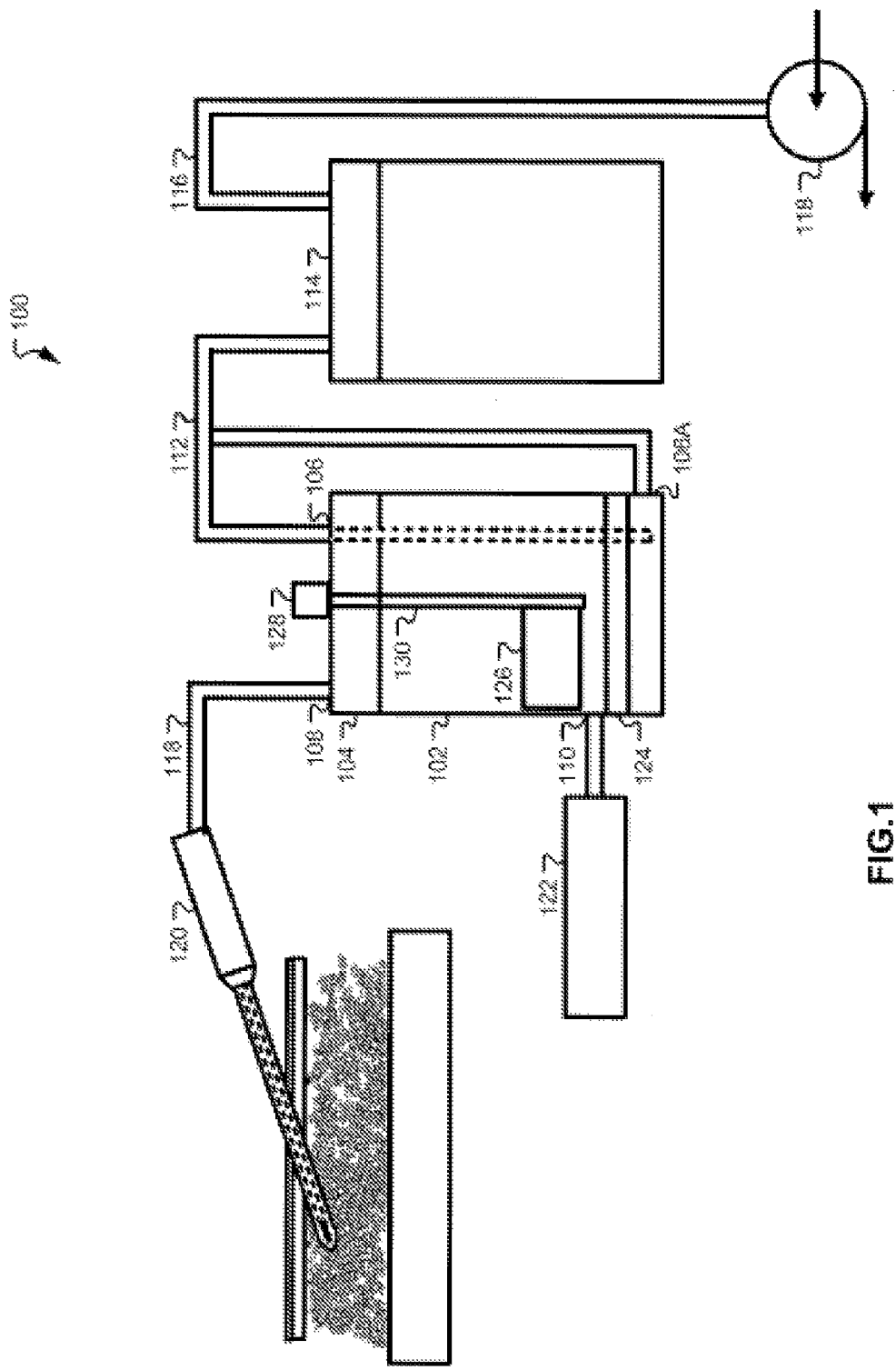
FIG. 1 illustrates a block diagram showing a system that incorporates a canister for AFT consistent with an embodiment of the present invention.
Figure 2:
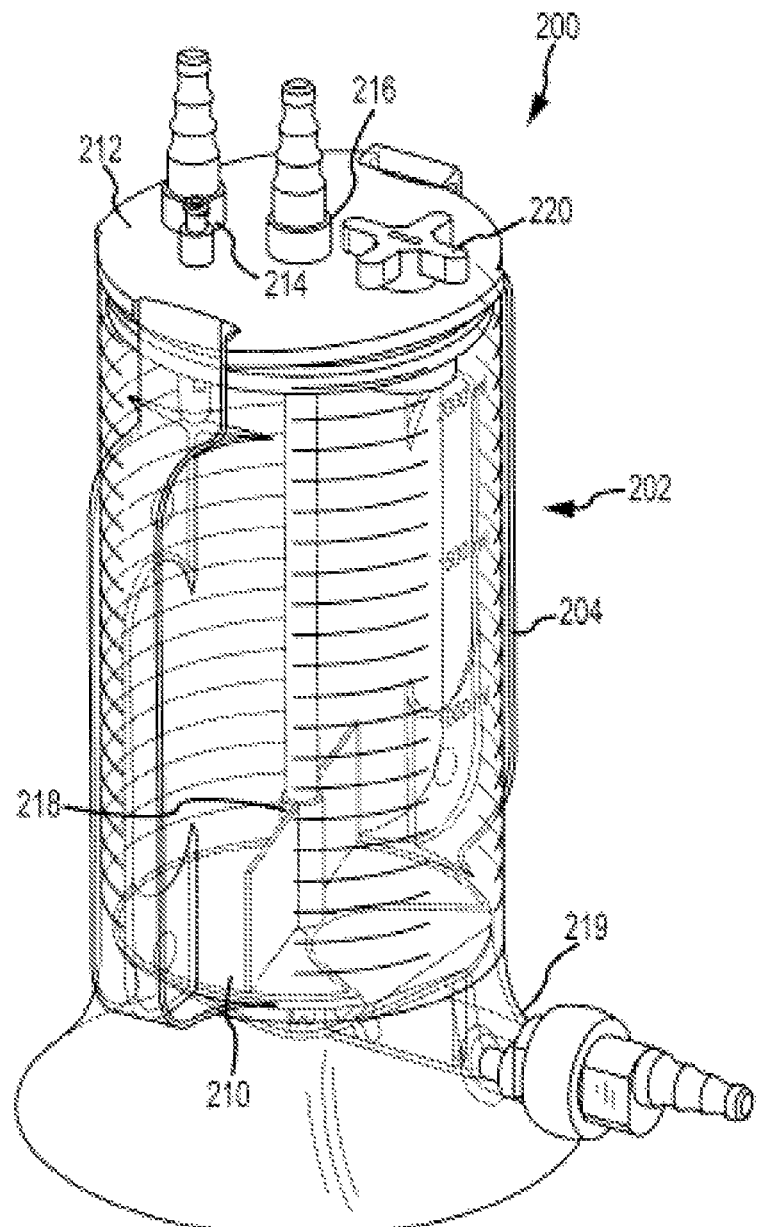
FIG. 2 illustrates a perspective view of a canister that is a first embodiment of the present invention.
Figure 3:
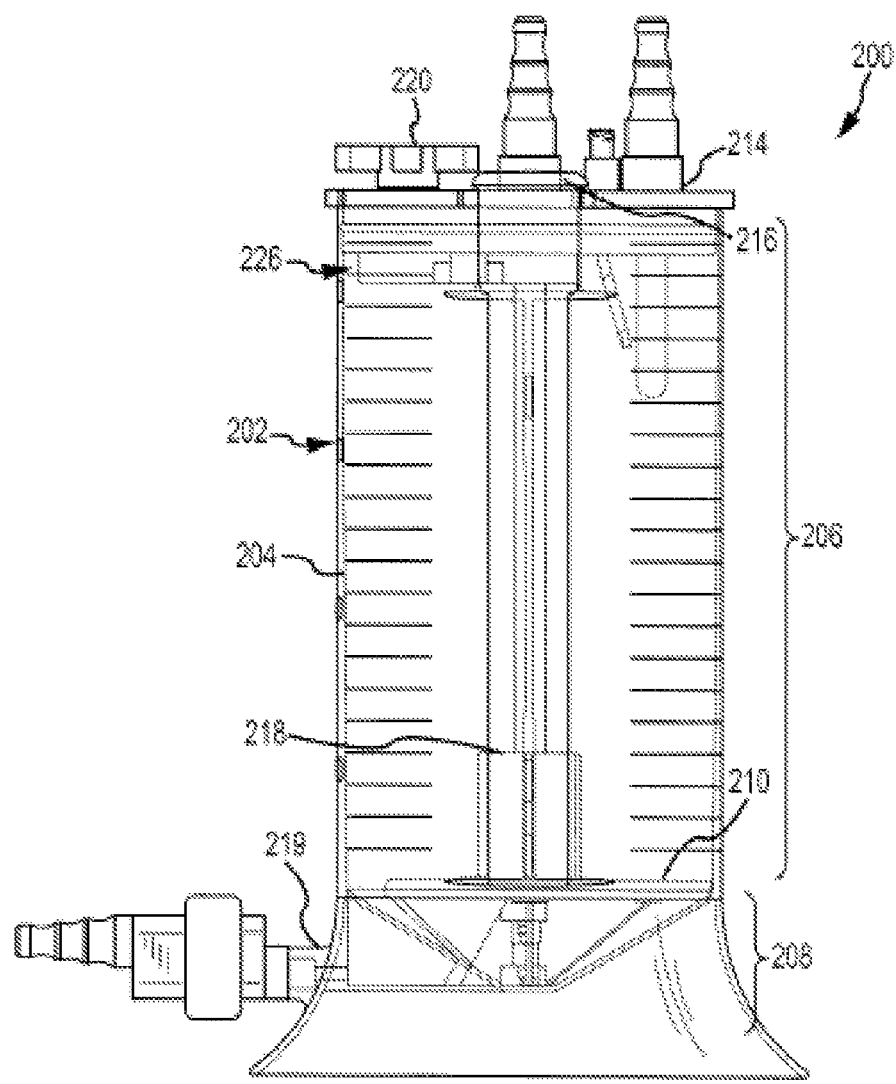
FIG. 3 illustrates a side view of the canister shown in FIG. 2.
Figure 4:
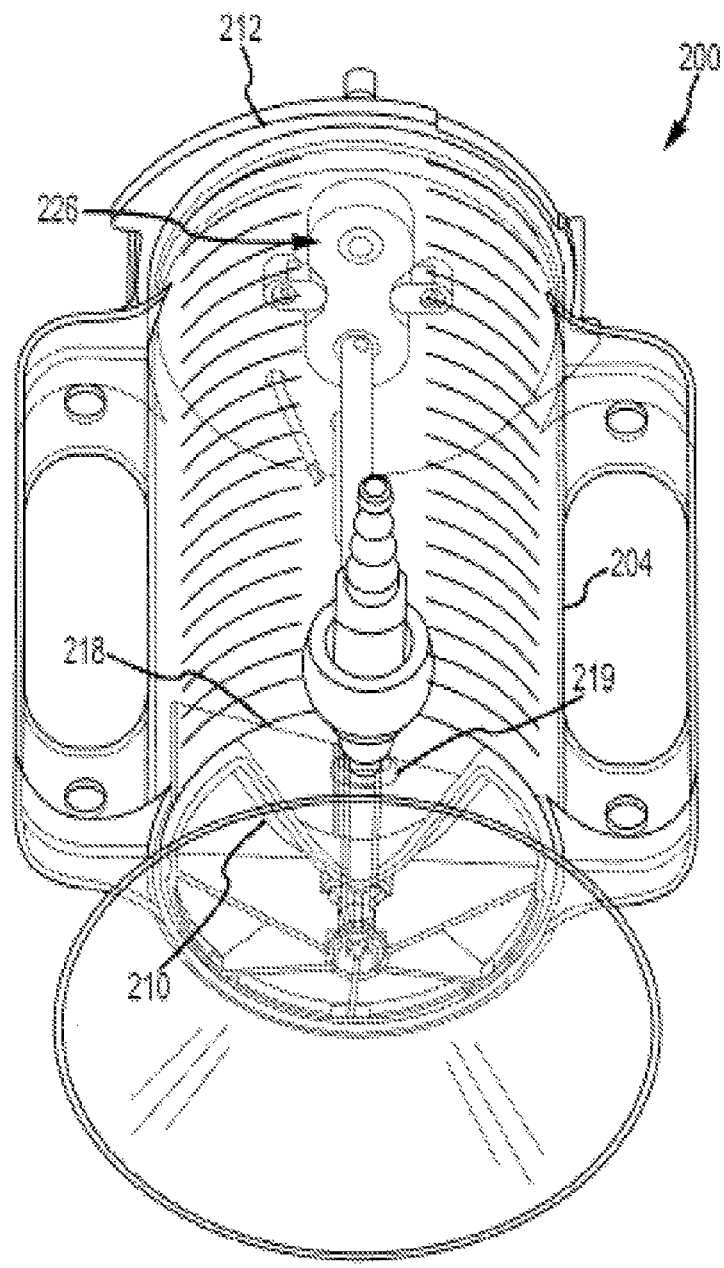
FIG. 4 illustrates a bottom perspective view of the canister shown in FIG. 2.
Figure 5:
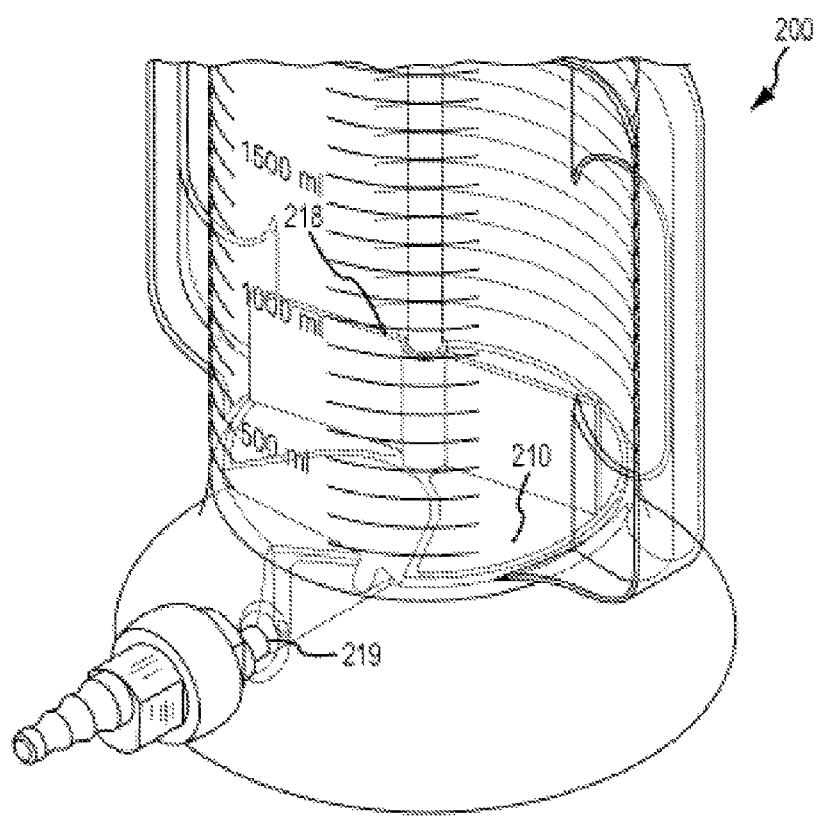
FIG. 5 illustrates a close up view of the filter of the canister shown in FIG. 2.

FIG. 1 illustrates a system 100 that incorporates a canister 102 according to an embodiment of the present invention. System 100 is used in Autologous Fat Transfer (AFT). As shown in FIG. 1, system 100 includes the canister 102, which includes a top 104, a first port 106, a second port 108, and an outlet port 110. Tubing 112 is connected to the first port 106. A second end of tubing 112 is connected to a liquid waste canister 114 where liquid removed from canister 102 is collected. Also connected to the liquid waste canister 114 is tubing 116 which is connected to a vacuum pump 118. A filter 124 is located within canister 102. Also inside canister 102 is a paddle 126 with at least one vane, which is connected to a rotational means 128 through shaft 130. Rotational means 128 can be used to move paddle 126 and agitate any tissue within canister 102 that is above filter 124. It is noted that rotational means 128 can be any suitable mechanism, and include a variety of structures, for rotating shaft 130 and paddle 126. In embodiments, rotational means 128 includes one or more of a knob, a handle, a grip, a motor, gears, shafts, and couplers.

Although first port 106 and second port 108 are shown as ports in top 104, they are not limited to this location. In other embodiments, the ports may be located on a sidewall of canister 102. For example, 106A shows an alternative location for the first port 106. Similarly, knob 128 may be located adjacent a sidewall of canister 102 instead of adjacent top 104. FIGS. 2-13 described below illustrate other embodiments with different designs.

In operation, vacuum pump 118 creates a vacuum within canister 114. The vacuum draws liquid from the bottom of canister 102, below the filter 124, and creates a vacuum within canister 102. The second port 108 is connected to tubing 118, which in turn is connected to a cannula 120 that is used to remove lipoaspirate, which includes fat, from a patient. The lipoaspirate travels through tubing 118, port 108, and into the canister 102. The lipoaspirate is filtered by filter 124 so that liquid such as blood or any other solutions in the lipoaspirate are separated from the fat and are removed by being drawn from the bottom of canister 102, below filter 124, through the first port 106. Knob 128 can be used to move paddle 126 to agitate the lipoaspirate and further separate liquid from the fat. The filtered fat can then be used to fill syringe 122, which is connected to outlet valve 110.

As can be appreciated from FIG. 1, in embodiments, canister 102 allows lipoaspirate removed from the patient to be continuously filtered and the fat in the lipoaspirate used to fill syringes for reinjection into a patient. The filtering of the fat and the filling of the syringes for reinjection occur even while fat is being removed from the patient with cannula 120. This can potentially reduce the overall amount of time that an AFT procedure takes.

FIG. 1 is merely intended to provide an overview of a system in which a canister (e.g., canister 102) consistent with an embodiment of the present invention is used. The description and illustration of system 100 in FIG. 1 is not intended to limit embodiments of the present invention. As described in greater detail below and shown in FIGS. 2-13, embodiments of the present invention may include features that are different than those described with respect to canister 102.

FIGS. 2-5 show various views (perspective, side, bottom perspective, and perspective close up) of one embodiment of a canister 200 of the present invention. The figures show the overall device 200, comprising the container 202 with a side wall 204 that defines a volume. The volume includes a top portion 206 and a bottom portion 208 which are separated by a filter 210 (see FIG. 3). The canister 200 also includes a top 212 that engages a top surface of side wall 204, an aspiration port 214 in fluid communication with the top portion 206, a vacuum port 216 in fluid communication with the bottom portion 208, a stirring paddle 218 with two vanes, and a knob 220 used as a handle for manually turning the paddle 218. When top 212 is engaged with the top surface of side wall 204, a seal is created that allows negative pressure to be maintained with the volume. The seal may be created between an inside surface of side wall 204 and top 212, or between a top surface of side wall 204 and top 212. The seal may include additional structures or materials, such as a gasket, o-ring, or a layer of other material. Canister 200 also includes an outlet port 219 in fluid communication with the top portion 206 for removing fat from the top portion 206 of the volume of the canister 200.

Figure 6:
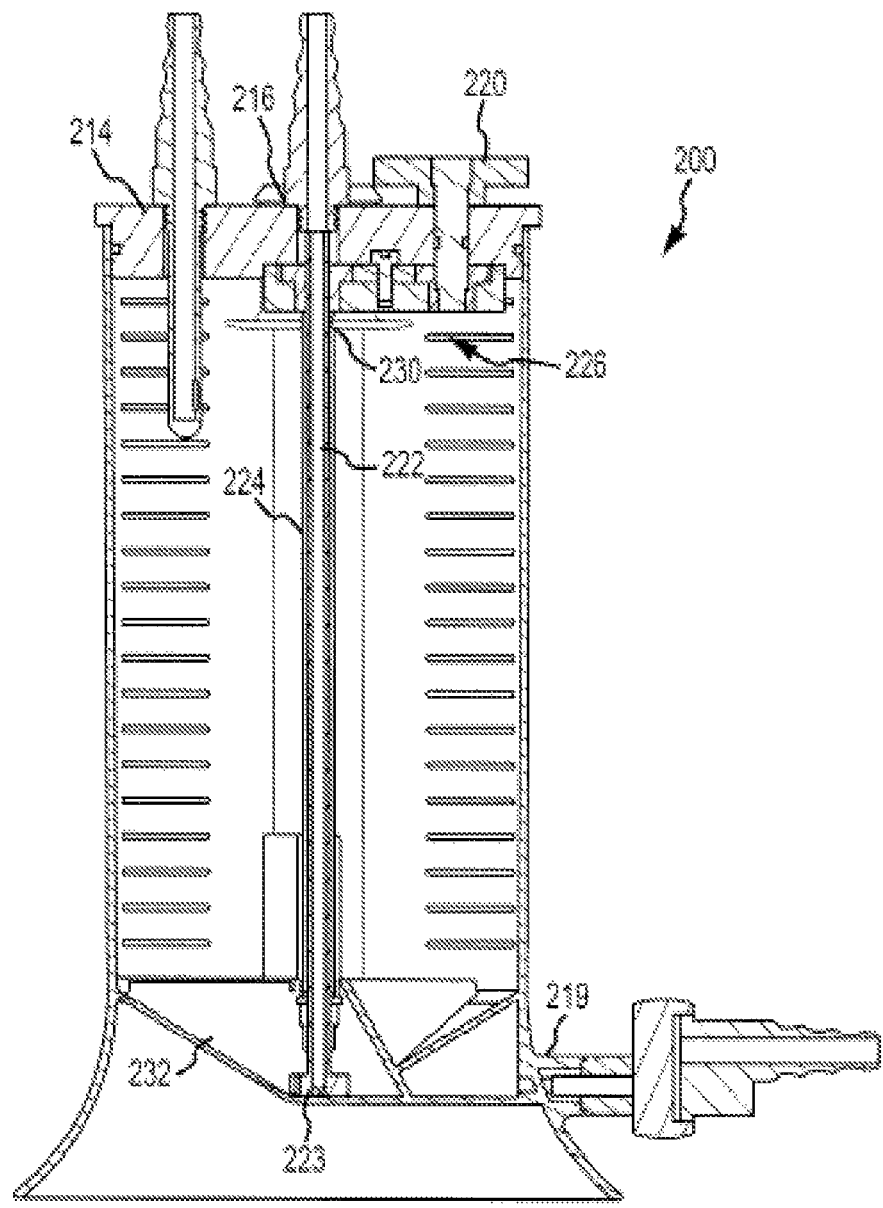
FIG. 6 illustrates a cross sectional view of the canister shown in FIG. 2.

FIG. 6 shows a cross-sectional view of canister 200. It shows details of a central vacuum tube 222 that is connected to the vacuum port 216. The central vacuum tube 222 includes perforations 223 at a distal end of tube 222, which is located at the bottom of the container within the bottom portion 208 of the volume. The perforations 223 create fluid communication between the central vacuum tube 222 and the bottom portion 208. When a vacuum is created within the central vacuum tube 222, a vacuum is also created in the bottom portion 208 and liquid is drawn into the central vacuum tube 222.

A concentric paddle tube 224 connects paddle 218 to knob 220 and translates rotation of knob 220 into rotation of paddle 218. As shown in FIG. 6, the central vacuum tube 222 is positioned within the concentric paddle tube 224. Gears 226 translate the rotation of knob 220 into rotation of the tube 224 and paddle 218. In other embodiments, knob 220 is directly connected to tube 222 eliminating the need for gears 226.

Tube 224 allows a space between its inner diameter and the outer diameter of vacuum tube 222. Tube 224 is configured to allow fluid communication, for vacuum balance, between the bottom portion of the volume 208 and the top portion of the volume 206. The fluid communication occurs using the space between the inner diameter of tube 224 and the outer diameter of vacuum tube 222. Also, tube 224 includes perforations 230 to allow the fluid communication. Also, shown in FIG. 6 is the plate structure 232 of the filter 210.

Canister 200 can be incorporated into a system that includes an aspiration cannula, interconnection tubing, a waste/disposal canister, and a vacuum source, e.g., system 100 of FIG. 1. In one example for using canister 200, the entire assembly of canister 200 is first sterilized using an autoclave or similar device. The canister 200 is then assembled as shown in FIGS. 2-6. A flexible tube is connected to the aspiration port 214 and the other end of the tube is connected to the aspiration cannula which will eventually be placed within a patient. A vacuum source is connected via a flexible tube to a disposal canister, which in turn is connected via another flexible tube to the vacuum port 216 of canister 200.

When the vacuum source is activated, lipoaspirate will be drawn from the patient via the aspiration cannula, through the tubing, and into the aspiration port 214. In embodiments, the vacuum source may provide about 15 inHg of vacuum. The internal part of the aspiration port 214 is designed so that the lipoaspirate is directed against the sidewall 204 of the container 202. This allows solid material in the lipoaspirate to break up, increasing the surface area of the lipoaspirate and hastening the separation of fat from the liquids. The fluid that passes through the filter 210 is removed via the central vacuum tube 222 to the disposal canister.

After the lipoaspirate is directed onto the sidewall 204 of the container 202, it falls onto the filter 210, which as noted above separates the bottom volume 208 from the top volume 206 of the container 202. Because a vacuum is being applied to the bottom volume 208 via the central vacuum tube 222, the fat is rapidly dewatered. This process is abetted by the movement of the paddle 218. The paddle is manually turned using the knob 220 on the lid of the canister 200. Note that the paddle 218 is shown with flat surfaces and including two vanes. Once the fat in the lipoaspirate has been sufficiently dewatered, it can be moved into a reinjection syringe connected to the outlet port 219 at the bottom of the container 202. The fat can then be reinjected into a patient.

As can be appreciated by those skilled in the art, paddle 218 in some embodiment will have other paddle configurations. For example, in some embodiments, paddle 218 has only one vane, while in other embodiments it has more than two vanes. Also, the vanes may have different shapes and include different curved surfaces. In one embodiment, paddle 218 includes at least one vane that is curved to direct the fat downwards toward filer 210. The knob 220 communicates mechanical motion to the paddle tube 224 via the gears 226. The gears 226 in the embodiment shown in FIGS. 2-6 are removable for later sterilization.

In embodiments, the paddle 218 can be positioned so that the vanes of the paddle scrape along the top surface of filter 210. In other embodiments, the vanes of paddle 218 are not in contact with the top surface of the filter 210 to avoid damage to the fat cells which might occur by being smashed between the vanes of the paddle 218 and the top surface of the filter 210.

In some embodiments, a bottom edge of paddle 218 is designed to be flexible to easily deform when tissue is positioned between the bottom edge of paddle 218 and the top surface of the filter 218. The flexible edge may be made of a soft material such as rubber or include other features, such as bristles, that allow the edge to more easily deform.

In some embodiments, the paddle 218 is moved using a motor. The motor can be directly connected to tube 224 or may be connected using one or more gears, shafts, fasteners, and other structures. The motor may have a variety of speeds that may be selected by a user and be configured to start and stop automatically. In other embodiments, the paddle 218 could also be moved by vacuum, using the same vacuum, as a source of motive power, used to remove the liquids from the bottom volume 208.

Figure 7:
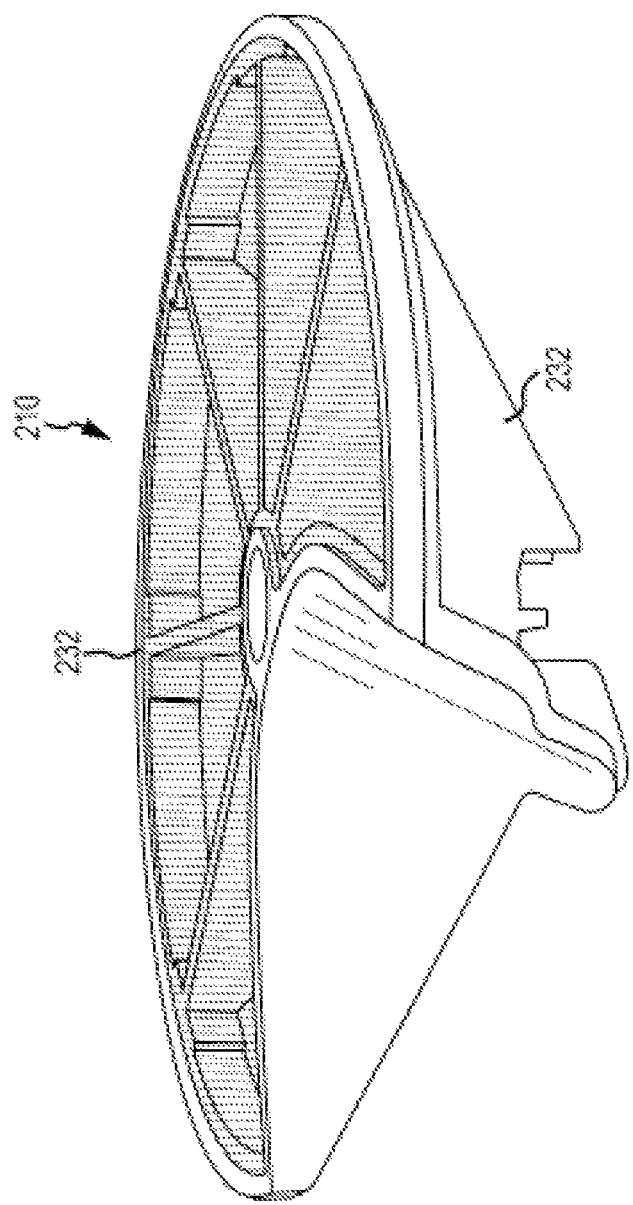
FIG. 7 shows a perspective view of one embodiment of a filter used in the canister of FIG. 2.

The filter 210, as shown in FIG. 7 has a portion that does not include perforations for filtering out liquid. This portion has a curved surface that directs fat toward outlet port 219. In other embodiments, this portion does include perforations for filtering lipoaspirate. FIG. 7 also shows the plate structure 232 of the filter 210. Plate structure 232 is used to provide structural integrity to filter 210 and ensure that it can withstand a large amount of lipoaspirate on its top surface without failing.

In some embodiments, canister 200 may also include a door that covers the exit region near outlet port 219, while the filtering is occurring. The door can be opened (e.g., lifted/slid) to allow the paddle 218 to push the fat into an exit region and into a syringe. The door could be manipulated using the central vacuum shaft 222.

Applying too strong of a vacuum on the lipoaspirate can in some situations cause damage to the cellular structure of the fat. Therefore, in some embodiments there is a means provided to limit the vacuum applied. This is accomplished by the perforations 230 in the paddle tube 224. These perforations 230 are located above where an expected total amount of lipoaspirate, to be contained within the canister 200, would reach.

As illustrated in FIG. 6, the paddle tube 224 extends from bellow the filter 210 to just below the lid 212. Tube 224 provides the pathway for air to balance between the bottom volume 208 below the filter 210 and the top volume 206 above the filter 210. When the canister 200 has material in it and the bottom volume 208 is full enough to cover the entire filter 210, the perforations 230 at the top of tube 224 let air flow from the top volume 206 of the canister 200 to the bottom volume 208 below the filter 210. This flow of air ensures that the pressure above the filter 210 is never too strong, causing damage to the filter, and the surgeon can continue the procedure without interruption of suction caused by the filter 210 being covered with material. The perforations 230 are designed so that there is a predetermined pressure difference between the top volume and bottom volumes. The air flow between the volumes does not cause any contamination issues, which may result in infections.

As those with skill in the art will appreciate, the size of the perforations 230 are such that a balance is reached between the rate of dewatering of the lipoaspirate, damage to the fat cells, and the size of the opening in the screen that is part of the filter 210. As noted above, the filter may include different sized openings such as between about 200 microns and about 1000 microns and in some embodiments between about 400 to about 700 micron sized openings. Some nonlimiting examples of opening sizes include about 432 microns, about 500 microns, or about 533 microns.

The size of the opening in the screen that is part of filter 210 is chosen based on a number of considerations including the preference of a surgeon and the ultimate location on the patient for the reinjection of fat. For instance, injections to the face require very little fat (on the order of several cubic centimeters), but there is little tolerance for any blood or other liquid from the lipoaspirate in the injection material. On the other hand, injections to the buttocks may involve several hundred cubic centimeters of fat, and there is more tolerance for some level of liquid in the injection material. Thus, each surgeon may select a specific screen with openings that are appropriate to their needs. Furthermore, in some embodiments, filter 210 includes a means for providing an adjustable opening size, such as a mechanism for sliding a screen with one size of opening over a screen of with a second size of openings.

Figure 8:
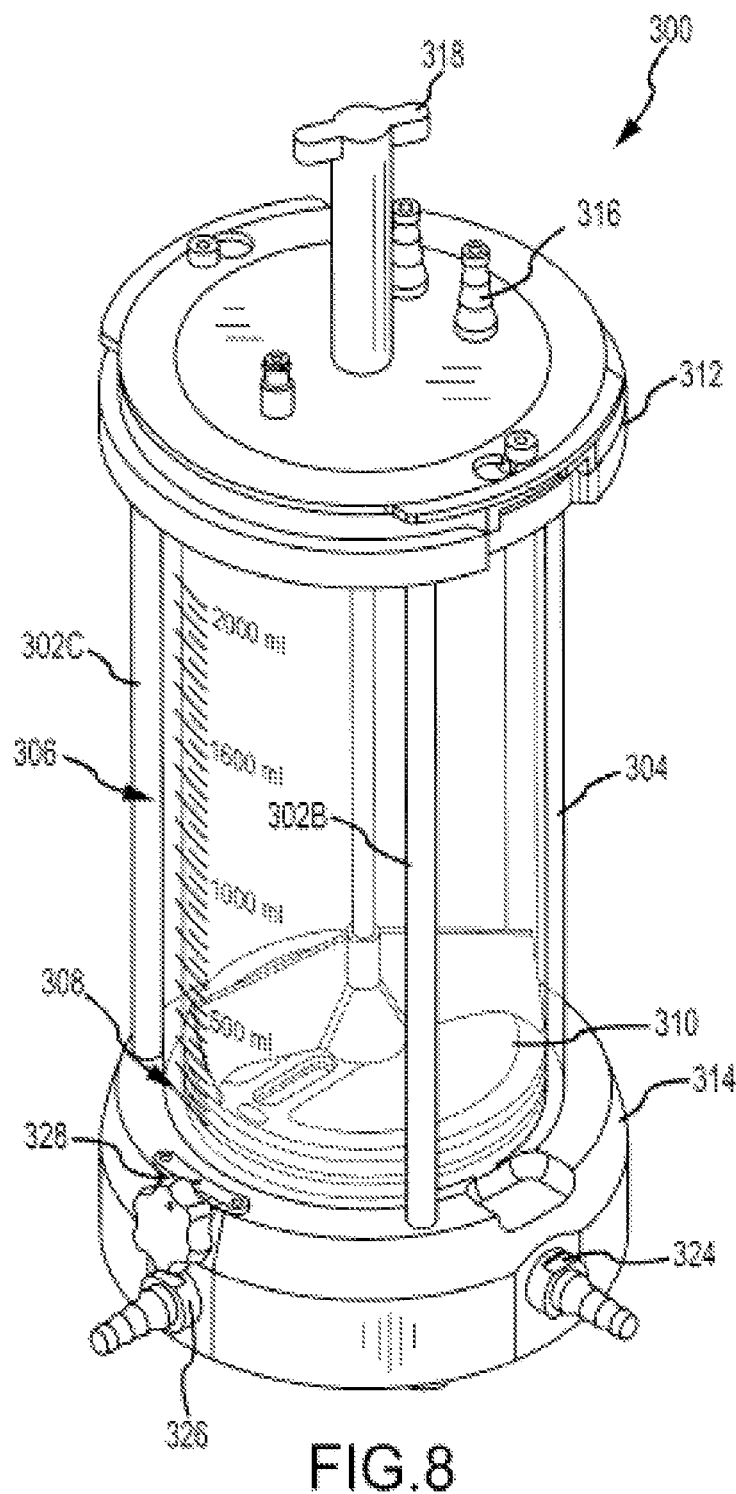
FIG. 8 illustrates a perspective view of a canister that is a second embodiment of the present invention.

FIGS. 8-12 illustrate various views of another embodiment of a canister 300. The figures illustrate the overall canister 300, as well as other views with different portions of canister 300 hidden to show particular features. As shown in FIG. 8, canister 300 has a caged design that includes rods 302A-C. Canister 300 also includes a side wall 304 that defines a volume for holding lipoaspirate. The volume includes a top portion 306 and a bottom portion 308 which are separated by a filter 310. In canister 300, the bottom portion 308 is located in a base 314.

Figure 9:
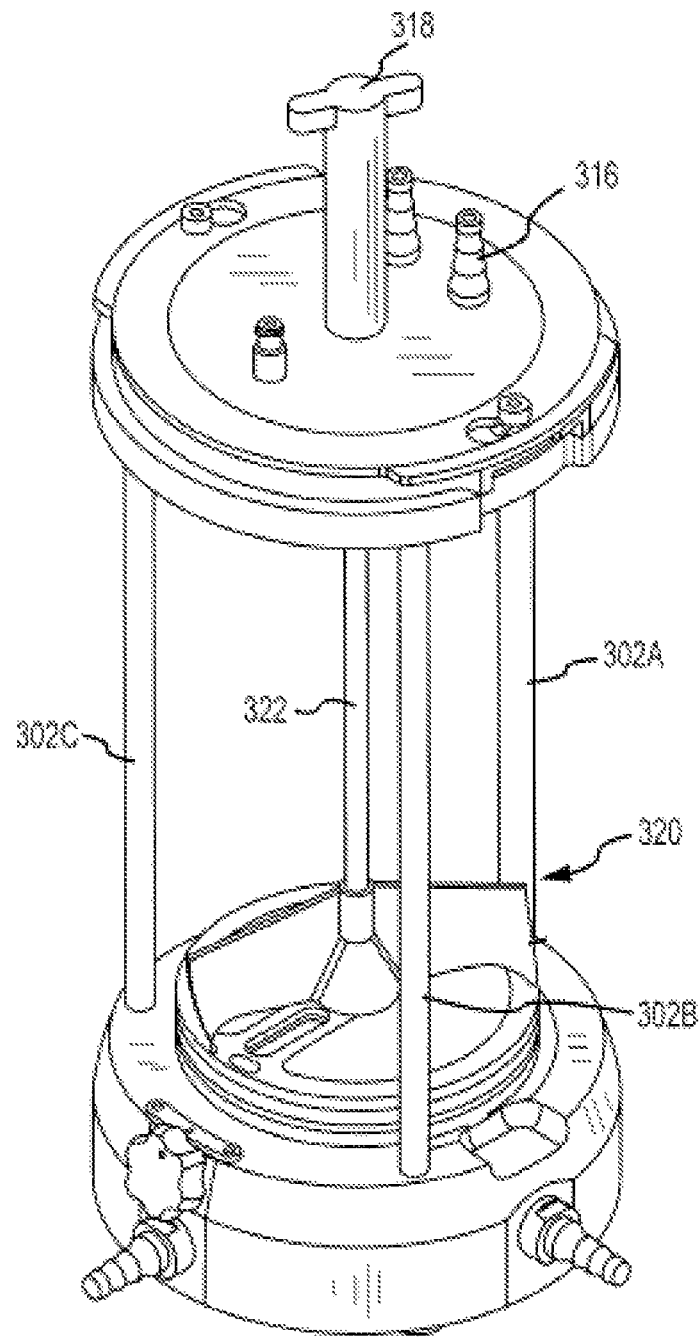
FIG. 9 illustrates a perspective view of the canister of FIG. 8 with a sidewall of the canister hidden.

Additionally, canister 300 includes a top 312 and the base 314 that engage the side wall 304 to further define the volume. The top 312 includes an aspiration port 316 and a handle 318. The handle 318 is used to manually turn paddle 320, which is positioned within the volume of canister 300. FIG. 9 illustrates a perspective view of canister 300 without the sidewall 304. FIG. 9 more clearly illustrates that handle 318 is connected to paddle 320 using shaft 322. The base 314 includes a vacuum port 324, and an outlet port 326. A valve 328 on base 314 is used to control flow of filtered fat through outlet port 326.

Canister 300 includes features that are similar to canister 200 with some design differences. As one example, the vacuum port 324 is located in base 314 instead of a lid or top as in canister 200. This design eliminates the need to have a tube for moving liquids from a bottom portion of the volume of a canister to the vacuum port located on the top. Accordingly, in canister 300, liquids that are filtered from the lipoaspirate and flow into the bottom volume 308 are directly removed from the bottom volume 308.

As is illustrated in FIGS. 8 and 9, paddle 320 includes two vanes, however in other embodiments; it may include a single paddle or more than two paddles. Each vane of paddle 320 includes a curved surface that helps to move the lipoaspirate when paddle 320 is rotated. The specific design shown in FIGS. 8 and 9 has a curved wedge-like shape that moves material from the bottom the vane to the top of the vane. This assists in agitating the lipoaspirate and to more quickly and completely separate the liquid from the fat. It is noted that the curved surfaces on the vanes of paddle 320 are used merely for illustrative purposes. In other embodiments, the vanes of paddle 320 may include surfaces with different shapes and sizes that are useful in agitating the lipoaspirate.

In embodiments, shaft 322 is hollow to allow fluid communication, for vacuum balance, between the bottom portion 308 and the top portion 306 of the volume. As noted above, applying too strong of a vacuum on the lip aspirate can in some situations cause damage to the cellular structure of the fat. Having an additional fluid communication channel prevents damage to the fat that may occur if the filter 310 becomes clogged. In addition to being hollow, shaft 322 may include perforations on a top end, above where an expected total amount of total lip aspirate, to be contained within the canister 300, would reach. Shaft 322 may, in some embodiments, be open at a bottom end (below the filter 310), or closed and include perforations that allow fluid to travel into the hollow shaft 322. The hollow shaft 322 and the perforations (on the top end and/or bottom end of shaft 322) provide an additional fluid communication channel allowing air or other gas to travel between the top portion 306 and the bottom portion 308 of the volume. Additionally, canister 300 may include one or more mechanisms for opening and closing the perforations to control the fluid communication between the top portion 306 and the bottom portion 308 of the volume.

Figure 13:
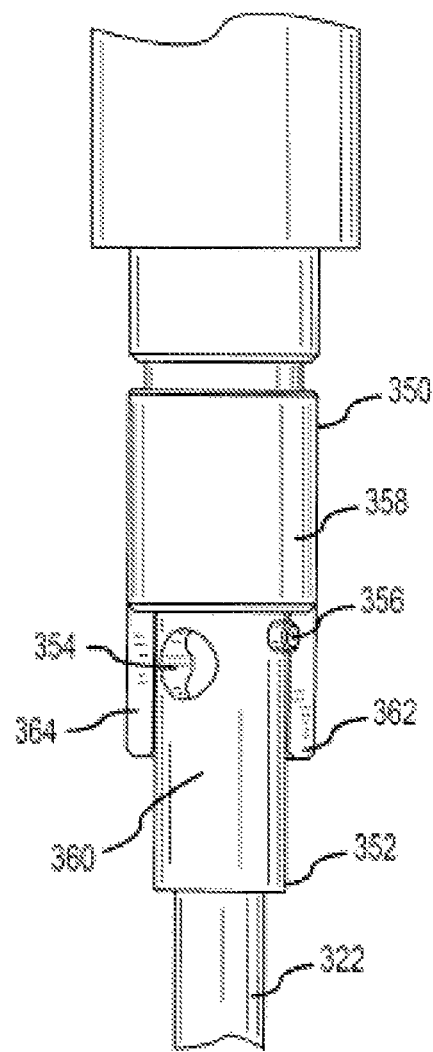
FIG. 13 illustrates a perspective view of an embodiment of a mechanism that can be used to control the fluid communication between a top portion and a bottom portion of a volume.

FIG. 13 illustrates a perspective view of an embodiment of a mechanism that can be used to control the fluid communication between the top portion 306 and the bottom portion 308 of the volume. Shown in FIG. 13 is a connection between two couplers 350 and 352. Coupler 350 is connected to a rotating means, e.g., handle 318, knob 220, or an electric motor. Coupler 352 is connected to hollow shaft 322. As shown in FIG. 13, coupler 352 includes a perforation 354 that allows fluid to enter and exit hollow shaft 322. Coupler 354 also includes a pin 356.

Coupler 350 includes an opening 360 in a portion of its side wall 358. As is shown in FIG. 13, when coupler 350 is connected to coupler 352, the pin 356 is positioned within opening 360. Additionally, when coupler 350 is connected to coupler 352, coupler 350 can rotate clockwise and counter clockwise about a central axis of coupler 352. As illustrated in FIG. 13, when the rotating means rotates coupler 350 in a clockwise direction, fluid is free to enter hollow shaft 322 through perforation 354. Pin 356 also engages portion 362 of side wall 358 which causes shaft 322, and any vanes or paddles connected to shaft 322, to rotate clockwise. When the rotating means rotates coupler 350 in a counter clockwise direction, perforation 354 is covered by a portion of side wall 358. Pin 356 engages portion 364 of side wall 358 which causes shaft 322, and any vanes or paddles connected to shaft 322, to rotate counter clockwise.

It is noted that FIG. 13 describes only one embodiment of a mechanism for controlling the fluid communication between a top portion of a volume and a bottom portion of a volume in a canister. In other embodiments, different structures (including a different channel) may be used in addition to, or in lieu of, the features shown in FIG. 13.

Figure 10:
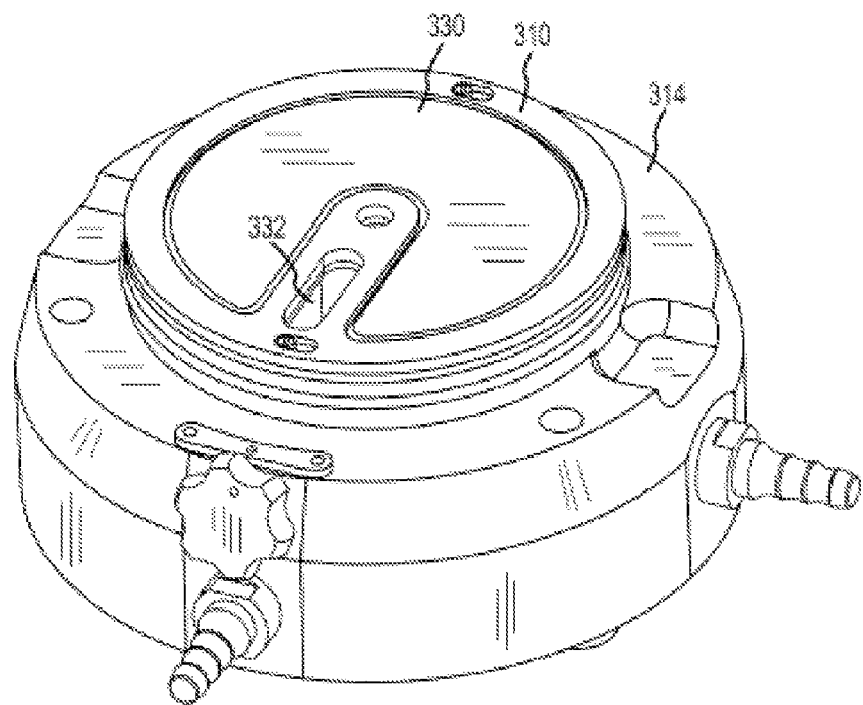
FIG. 10 illustrates a perspective view of a base of the canister shown in FIG. 8.
Figure 11:
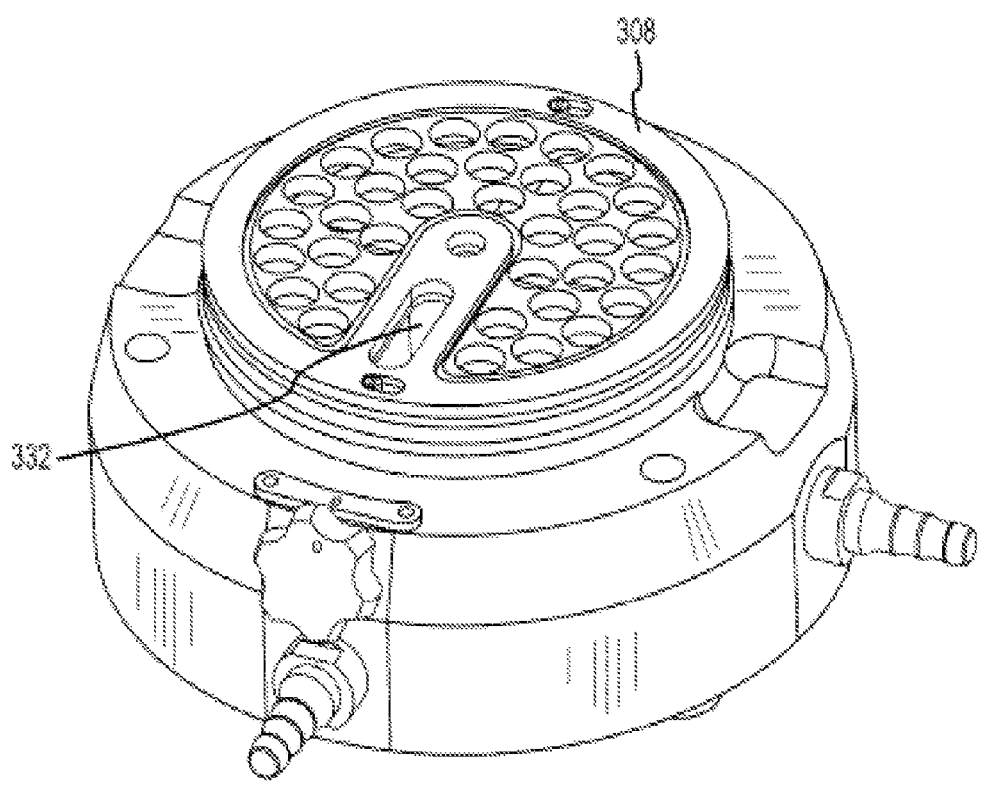
FIG. 11 illustrates a perspective view of the base of the canister shown in FIG. 8 with a filter that does not include a screen.
Figure 12:
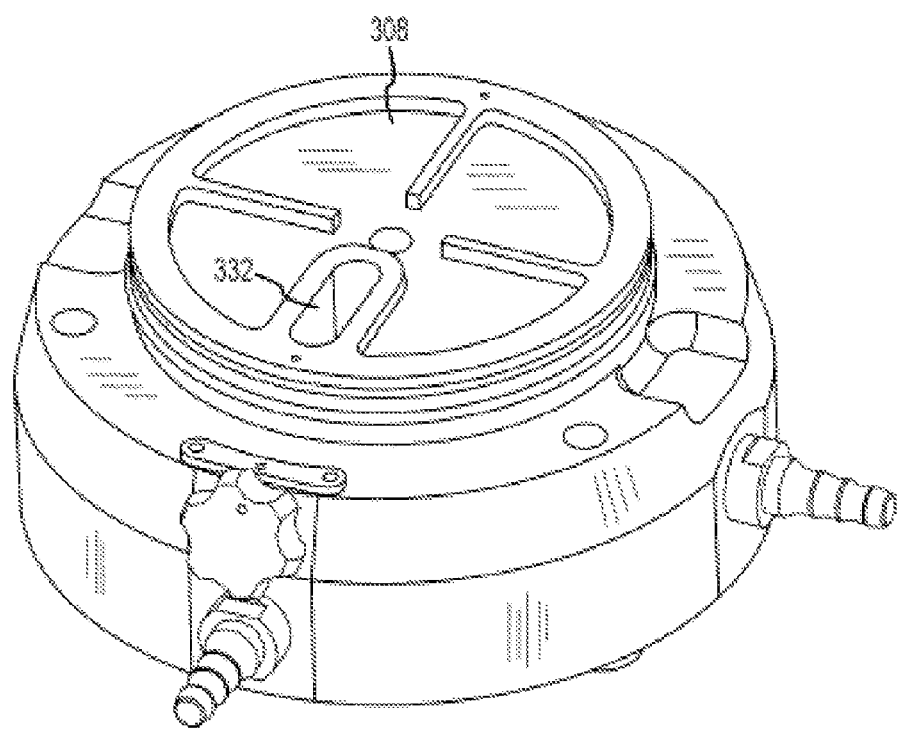
FIG. 12 illustrates a perspective view of the base of the canister shown in FIG. 8 without a filter.

FIGS. 10-12 illustrate features of filter 310 and base 314 in more detail. FIG. 10 shows a perspective view of base 314 with other features of canister 300 hidden. FIG. 11 illustrates a similar view as FIG. 10 but with a screen 330 of filter 310 hidden. FIG. 12 provides and illustration with the filter 310 hidden.

When canister 300 is in use, lipoaspirate is moved over the surface of screen 330 by paddle 320. The movement of the lipoaspirate separates the liquids from the fat. The liquids fall into the bottom portion 308 of the volume (see FIG. 12). The liquids in the bottom portion 308 are removed through the vacuum port 324.

After the lipoaspirate has been sufficiently dewatered, valve 328 can be opened to allow the fat to be removed from canister 300, e.g., into a syringe for reinjection. As illustrated in FIGS. 10-12, the treated fat flows through an exit channel 332 in base 314. The exit channel 332 is in fluid communication with the outlet port 326.

In embodiments, screen 330 can be separated from filter 310 to allow for use of screens with different sized openings. In other embodiments, the screen 330 may be attached to filter 310 and require removal of filter 310 if a screen with different sized openings is desired. The screen 330 may also have different dimensions. Some examples of screen sizes and the size of the openings include, without limitation, 20 wires per inch×20 wires per inch with 864 micron openings; 35 wires per inch×35 wires per inch with 457 micron openings; 30 wires per inch×30 wires per inch screen with 533 micron openings; 28 wires per inch×28 wires per inch screen with 660 micron openings; and 40 wires per inch×40 wires per inch with 381 micron openings.

Canister 300 provides additional features not included in canister 200. For example, valve 328 allows a surgeon additional control over the volume of material, namely treated fat, that flows through outlet port 326. Canister 300 also is easier to sterilize since the top 312, side wall 304, and the base 314 can be separated from each other. The ability to disassemble canister 300 also allows parts that fail to be replaced. It is noted that when top 312 is engaged with side wall 304, a seal is created that allows negative pressure to be maintained within the volume. Additionally, a second seal is created when base 314 is engaged with side wall 304. The second seal also allows negative pressure to be maintained within the volume. The seals may be created between an inside surface of side wall 204 and top 312 (or base 314), or between a top surface of side wall 304 and top 312 (or base 314). The seals may include additional structures or materials, such as a gasket, o-ring, or a layer of other material.

Canisters 200 and 300 provide a number of features useful in AFT. For example, they provide a "closed" system allowing syringes of fat for reinjection to be prepared while lipoaspirate is being removed from a patient. A surgeon therefore does not have to interrupt the aspiration process while the fat is processed and extracted into syringes. In some embodiments, a surgeon does remove the cannula from the patient or otherwise vent the aspiration cannula to allow the syringe filling to proceed. However, a vented cannula, such as those supplied by Sound Surgical Technologies, of Louisville, Colo. permits sufficient flow to allow filling of syringes during aspiration. Embodiments of the present invention allow continuous separation of fat from lipoaspirate and placement of the fat into syringes without interruption of the aspiration process. The embodiments also provide the ability to process fat in a "closed" fashion while still providing manual manipulation of the fat, and the ability to process any amount of fat required simply by using larger canisters and by removing fat via syringe while the fat is being aspirated from a patient.

While the present invention has been described in relation to specific embodiments, it is not limited thereto. In other embodiments, there may be additional features that are included as part of a canister or as part of a system that utilized the canister. For example, in some embodiments a prefilter is used to catch large strands of fat in the lipoaspirate, before the lipoaspirate is filtered by a filter, e.g. filter 210 (FIGS. 2-7) or filter 310 (FIGS. 8-11). A prefilter can be useful in situations in which fat is being removed from a patient by power assisted lipoplasty which tends to remove larger strands of fat. The pre-filter is in embodiments mounted inside a canister, such as surrounding the inlet port, or it can be a separate canister in line ahead of the canister. This is merely one example, and additional components can be added to a canister or a system using a canister to provide additional functionality that is within the scope of the present invention.

Reference has been made throughout this specification to "one embodiment" or "an embodiment," meaning that a particular described feature, structure, or characteristic is included in at least one embodiment. Thus, usage of such phrases may refer to more than just one embodiment. Furthermore, the described features, structures, or characteristics may be combined in any suitable manner in one or more embodiments. For example, features described with respect to the embodiments shown in FIGS. 2-7 may be combined with features of the embodiments shown in FIGS. 8-12.

One skilled in the relevant art may recognize, however, that the invention may be practiced without one or more of the specific details, or with other methods, resources, materials, etc. In other instances, well known structures, resources, or operations have not been shown or described in detail merely to avoid obscuring aspects of the invention.

While example embodiments and applications have been illustrated and described, it is to be understood that the invention is not limited to the precise configuration and resources described above. Various modifications, changes, and variations apparent to those skilled in the art may be made in the arrangement, operation, and details of the methods and systems disclosed herein without departing from the scope of the claimed invention.

We claim:

1. A canister for use in autologous fat transfer, the canister comprising:
   a side wall defining a volume;
   a filter that separates the volume into a top portion of the volume and a bottom portion of the volume;
   a vacuum port in fluid communication with the bottom portion of the volume;
   an aspiration port in fluid communication with the top portion of the volume, the aspiration port configured to receive lipoaspirate comprising fat and liquid;
   at least one vane positioned within the top portion of the volume, the at least one vane configured to be rotated relative to the filter; and
   an outlet port in fluid communication with the top portion of the volume, the outlet port configured to be coupled with a syringe for removing the fat from the top portion of the volume.

2. The canister of claim 1, further comprising:
   a base, configured to engage the side wall and to further define the volume.

3. The canister of claim 2, wherein the vacuum port is in the base.

4. The canister of claim 3, wherein the outlet port is in the base.

5. The canister of claim 1, further comprising:
   a top configured to engage the side wall and to further define the volume.

6. The canister of claim 5, wherein the vacuum port is in the top portion of the volume.

7. The canister of claim 6, wherein the aspiration port is in the top portion of the volume.

8. The canister of claim 1, wherein the at least one vane is part of a paddle.

9. The canister of claim 1, wherein the filter comprises a screen.

10. The canister of claim 1, wherein the screen comprises openings that are between 200 microns to 1000 microns.

11. A canister for use in autologous fat transfer, the canister comprising:
    a side wall defining a volume;
    a top engaged with the side wall to further define the volume and create a first seal with the sidewall;
    a base engaged with the side wall to further define the volume and create a second seal with the sidewall, wherein the first seal and the second seal allow a vacuum to be maintained with the volume;
    a filter that separates the volume into a top portion of the volume and a bottom portion of the volume;
    a vacuum port in fluid communication with the bottom portion of the volume;
    an aspiration port in fluid communication with the top portion of the volume, the aspiration port configured to receive lipoaspirate comprising fat and liquid;
    a paddle including at least one vane positioned within the top portion of the volume, the at least one vane configured to be rotated relative to the filter; and
    an outlet port in fluid communication with the top portion of the volume, the outlet port configured to be coupled with a syringe for removing the fat from the top portion of the volume.

12. The canister of claim 11, wherein the filter comprises a screen.

13. The canister of claim 11, wherein the screen comprises openings that are between 400 microns to 600 microns.

14. The canister of claim 11, further comprising:
    a valve in fluid communication with the outlet port, the valve configured to control the flow of the fat through the outlet port.

15. The canister of claim 11, further comprising:
    a handle external to the volume; and
    a shaft that connects the paddle to the handle.

16. The canister of claim 11, wherein the paddle comprises at least two vanes.

17. The canister of claim 11, wherein the at least one vane comprises at least one curved surface.

* * * * *